United States Patent [19]

Quadri et al.

[11] Patent Number: 5,792,759
[45] Date of Patent: Aug. 11, 1998

[54] 17-HYDROXYIMINOALKYL AND 17-HYDROXYIMINOMETHYLALKENYL CYCLOPENTANEPERHYDROPHENANTHRENE DERIVATIVES ACTIVE ON THE CARDIOVASCULAR SYSTEM, A PROCESS FOR THEIR PREPARATION AND PHARMACEUTICAL COMPOSITIONS CONTAINING THE SAME

[75] Inventors: Luisa Quadri, Cernusco sul Naviglio; Alberto Cerri, Gessate; Patrizia Ferrari, Varese; Maria Pia Zappavigna, Magenta, all of Italy

[73] Assignee: Sigma-Tau Industrie Farmaceutiche Riunite S.p.A., Rome, Italy

[21] Appl. No.: 648,962

[22] Filed: May 17, 1996

[30] Foreign Application Priority Data

Jun. 23, 1995 [IT] Italy .................... RM95 A 000421

[51] Int. Cl.[6] .................. C07J 41/00; C07J 43/00; A61K 31/58; A61K 31/575
[52] U.S. Cl. .................. 514/176; 514/182; 540/107; 540/108; 540/112; 552/552; 552/554; 552/555; 552/600; 552/601; 552/606; 552/607; 552/609; 552/611
[58] Field of Search .................. 552/552, 554, 552/555, 600, 601, 606, 607, 609, 611; 540/107, 108, 112; 514/176, 182

[56] References Cited

U.S. PATENT DOCUMENTS 4,490,296 12/1984 Barton et al. .................. 260/397.5
5,324,719 6/1994 Frigerio et al. .
5,444,055 8/1995 Cerri et al. .................. 514/182
5,538,960 7/1996 Cerri et al. .................. 514/176
5,583,127 12/1996 Cerri et al. .................. 514/175
5,599,806 2/1997 Cerri et al. .................. 514/174

*Primary Examiner*—Kimberly J. Prior
*Attorney, Agent, or Firm*—Oblon, Spivak, McClelland, Maier & Neustadt, P.C.

[57] ABSTRACT

Novel 17-hydroxyiminoalkyl and 17-hydroxyiminomethylalkenyl steroids of the general formula (I)

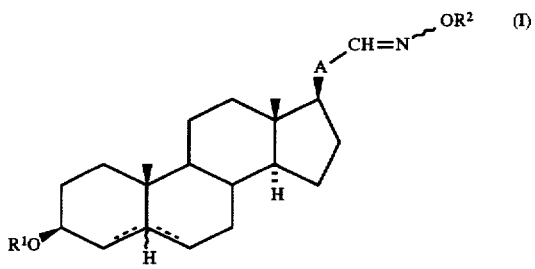

where A, $R^1$ and $R^2$ are defined in the specification are disclosed. The compounds have cardiovascular activity. Pharmaceutical compositions containing compounds of formula (I) are also disclosed for the treatment of heart failure and hypertension.

6 Claims, No Drawings

17-HYDROXYIMINOALKYL AND 17-HYDROXYIMINOMETHYLALKENYL CYCLOPENTANEPERHYDROPHENANTHRENE DERIVATIVES ACTIVE ON THE CARDIOVASCULAR SYSTEM, A PROCESS FOR THEIR PREPARATION AND PHARMACEUTICAL COMPOSITIONS CONTAINING THE SAME

The present invention relates to novel 17-hydroxyiminoalkyl and hydroxyiminomethylalkenyl cyclopentaneperhydrophenanthrene derivatives active on the cardiovascular system, a process for their preparation and pharmaceutical compositions containing same, for the treatment of cardiovascular disorders such as heart failure and hypertension.

Digitalis compounds such as 17-hydroxyiminomethyl-5β-androstan-3β-14β-diol (DE 4,227,626) have been reported to show good affinity for and inhibit the enzyme Na$^+$, K$^+$-ATPase.

The compounds claimed herein, even though they do not have the digitalis structure, surprisingly show high affinity for the receptor site of the Na$^+$, K$^+$-ATPase and are active on the cardiovascular system.

The compounds of the present invention have formula (I):

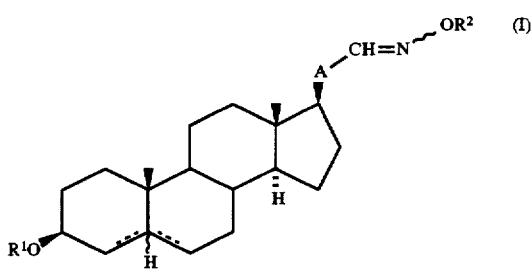

wherein: the symbol ~~~ represents either α or β configuration or a Z or E configuration;

A represents (CH$_2$)m, —(CH=CH)n— or —(CH=CR$^3$)—;

m is a whole number from 0 to 4;

n is 1 or 2;

R$^3$ represents methyl, ethyl or n-propyl.

R$^1$ represents H, C2–C4 alkyl unsubstituted or substituted by NR$^4$R$^5$ wherein R$^4$, R$^5$ are independently H, C1–C4 alkyl, or R$^4$ and R$^5$ can form with the nitrogen atom they are linked to, a saturated or unsaturated five- or six-membered monoheterocyclic ring optionally containing a further heteroatom selected from N and O;

R$^2$ represents C2–C4 alkyl, unsubstituted or substituted by NR$^4$R$^5$ or NHC(=NH)NH$_2$, wherein R$^4$ and R$^5$ have the above-specified meanings.

Should the compounds of formula (I) present themselves as distinct tautomeric forms, it should be understood that the foregoing formula encompasses also such forms; the formula encompasses all the stereoisomers, the Z and E isomers and mixtures thereof, the optical isomers and mixtures thereof.

Also encompassed within the scope of the present invention are the pharmacologically acceptable salts of the compounds of formula (I). By pharmacologically acceptable salts are meant those salts which retain the biological activity of the unsalified parent compound and are derived from such known pharmacologically acceptable acids such as e.g. hydrochloric, hydrobromic, sulfuric, phosphoric, fumaric, succinic, oxalic, malic, tartaric, maleic, citric, methanesulfonic or benzoic acid and others still which will be readily apparent to the average-skilled experts in pharmaceutical technology.

The compounds of the present invention also encompass the solvates such as the hydrates.

Also the N-oxydes on the tertiary nitrogen atoms are encompassed by the present invention.

The alkyl groups are straight or branched or cyclic groups.

The C2–C4 alkyl groups are preferably ethyl, n-propyl, isopropyl, n-butyl or ter-butyl.

The C1–C4 alkyl groups are preferably methyl, ethyl, n-propyl, iso-propyl, n-butyl or tert-butyl.

R$^1$ is preferably H, 2-aminoethyl, 3-aminopropyl, 2-dimethylaminoethyl, 3-dimethylaminopropyl, 2-diethylaminoethyl, 3-diethylaminopropyl, 2-(1-pyrrolidinyl)ethyl, 3-(1-pyrrolidinyl)propyl.

R$^2$ is preferably 2-aminoethyl, 3-aminopropyl, 2-dimethylaminoethyl, 3-dimethylaminopropyl, 2-diethylaminoethyl, 3-diethylaminopropyl, 2-(1-pyrrolidinyl)ethyl, 3-(1-pyrrolidinyl)propyl, 2-guanidinoethyl, 3-guanidinopropyl.

Preferred examples of specific compounds according to the present invention are:

(E)-17β-(2-aminoethoxyiminomethyl)-5β-androstan-3β-ol
(E)-17β-(3-aminopropoxyiminomethyl)-5β-androstan-3β-ol
(E)-17β-(4-aminobutoxyiminomethyl)-5β-androstan-3β-ol
(E)-17β-(2-dimethylaminoethoxyiminomethyl)-5β-androstan-3β-ol
(E)-17β-(3-dimethylaminopropoxyiminomethyl)-5β-androstan-3β-ol
(E)-17β-(4-dimethylaminobutoxyiminomethyl)-5β-androstan-3β-ol
(E)-17β-(2-guanidinoethoxyiminomethyl)-5β-androstan-3β-ol
(E)-17β-(3-guanidinopropoxyiminomethyl)-5β-androstan-3β-ol
(E,E)-17β-[3-(2-aminoethoxyimino)-1-propenyl]-5β-androstan-3β-ol
(E,E)-17β-[3-(3-aminopropoxyimino)-1-propenyl]-5β-androstan-3β-ol
(E)-17β-[3-(4-aminobutoxyimino)-1-propenyl]-5β-androstan-3β-ol
(E,E)-17β-[3-(2-dimethylaminoethoxyimino)-1-propenyl]-5β-androstan-3β-ol
(E,E)-17β-[3-(3-dimethylaminopropoxyimino)-1-propenyl]-5β-androstan-3β-ol
(E,E)-17β-[3-(2-guanidinoethoxyimino)-1-propenyl]-5β-androstan-3β-ol
(E,E)-17β-[3-(3-guanidinopropoxyimino)-1-propenyl]-5β-androstan-3β-ol
(E,E)-17β-[3-(2-aminoethoxyimino)-2-methyl-1-propenyl-5β-androstan-3β-ol
(E,E)-17β-[3-(3-aminopropoxyimino)-2-rmethyl-1-propenyl]-5β-androstan-3β-ol
(E,E)-17β-[3-(2-dimethylaminoethoxyimino)-2-methyl-1-propenyl]-5β-androstan-3β-ol
(E,E)-17β-[3-(3-dimethylaminopropoxyimino)-2-methyl-1-propenyl]-5β-androstan-3β-ol
(E,E)-17β-[3-(2-guanidinoethoxyimino)-2-methyl-1-propenyl]-5β-androstan-33β-ol
(E,E)-17β-[3-(3-guanidinopropoxyimino)-2-methyl-1-propenyl]-5β-androstan-3β-ol
(E,E)-17β-[3-(2-aminoethoxyimino)-2-ethyl-1-propenyl]-5β-androstan-3β-ol
(E,E,E)-17β-[5-(2-aminoethoxyimino)-1,3-pentadienyl]-5β-androstan-3β-ol (E,E,E)-17β-[5-(3-aminopropoxyimino)-1,3-pentadienyl]-5β-androstan-3β-ol (E,E,E)-17β-[5-(2-dimethylaminoethoxyimino)-1,3-pentadienyl]-5β-androstan-3β-ol (E,E,E)-17β-[5-(3-dimethylaminopropoxyimino)-1,3-pentadienyl]-5β-androstan-3β-ol (E,E,E)-17β-[5-(2-guanidinoethoxyimino)-1,3-pentadienyl]-5β-androstan-3β-ol (E,E,E)-17β-[5-(3-guanidinopropoxyimino)-1,3-pentadienyl]-5β-androstan-3β-ol (E)-17β-[2-(2-aminoethoxyimino)ethyl]-5β-androstan-3β-ol (E)-17β-[2-(3-aminopropoxyimino)ethyl]-5β-androstan-3β-ol (E)-17β-[2-(2-dimethylaminoethoxyimino)ethyl]-5β-androstan-3β-ol (E)-17β-[2-(3-dimethylaminopropoxyimino)ethyl]-5β-androstan-3β-ol (E)-17β-[2-(2-guanidinoethoxyimino)ethyl]-5β-androstan-3β-ol (E)-17β-[2-(3-guanidinopropoxyimino)ethyl]-5β-androstan-3β-ol (E)-17β-[3-(2-aminoethoxyimino)propyl]-5β-androstan-3β-ol (E)-17β-[3-(3-aminopropoxyimino)propyl]-5β-androstan-3β-ol (E)-17β-[3-(2-dimethylaminoethoxyimino)propyl]-5β-androstan-3β-ol (E)-17β-[3-(3-dimethylaminopropoxyimino)propyl]-5β-androstan-3β-ol (E)-17β-[3-(2-guanidinoethoxyimino)propyl]-5β-androstan-3β-ol (E)-17β-[3-(3-guanidinopropoxyimino)propyl]-5β-androstan-3β-ol and, if any, the Z and E isomers and their mixtures;
and the corresponding androstan -3β-ol, androst-4-en-3β-ol and androst-5-en-3β-ol of the aforesaid compounds;
and the corresponding 3β-(2-aminoethyl), 3β-(2-dimethylamino-ethyl), 3β-[2-(1-pyrrolidinyl)ethyl)], 3β-(3-aminopropyl), 3β-(3-dimethylaminopropyl) and 3β-(3-(1-pyrrolidinyl)propyl) ethers of the aforesaid compounds;

The invention further provides a process for the preparation of the compounds of formula (I), which comprises the condensation reaction of compounds of formula (II)

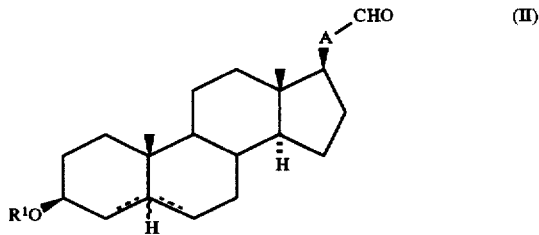

wherein A, R¹ and the symbol ⌇⌇ have the above-specified meanings, with compounds of formula (III)

wherein R² has the above-specified meaning, to give the compounds of formula (I).

Compounds of formula (III) can be used as free bases or as salts with an acid, e.g. hydrochloric, hydrobromic, hydriodic, carbonic, oxalic or sulfuric acid.

The reaction can be carried out in a solvent such as ethanol, methanol, acetonitrile, dioxane, tetrahydrofurane, water or a mixture of such solvents at a temperature ranging from 0° C. to the boiling point of the above-mentioned solvents or their mixtures.

Further salts such as $NaH_2PO_4$, $Na_2HPO_4$, NaOAc, or acids such as e.g. hydrocloric, hydrobromic, acetic, sulfuric, phosphoric and bases such as sodium or potassium hydroxyde can be added to the reaction mixtures, to maintain the selected pH.

The groups if any, present on R¹ are protected if necessary, with known methods to give, after removal of the protective groups, if any, compounds of general formula (I) which can be converted to other compounds of formula (I) with known methods.

The compounds of general formula (II) wherein A represents $(CH_2)m$, m is 0 and R¹ is H and the symbol ⌇⌇ represents either α or β configuration, are the known compounds: 3β-hydroxy-5β-androstan-17β-carboxyaldehyde Gelbart, A. et al., J. Med. Chem., 1978, 21(3), 284), 3β-hydroxyandrostan-17β-carboxyaldehyde (Paglialunga Pradisi, M., et al., Tetrahedron, 1982, 38, 1827), 3β-hydroxyandrost-4-en-17β-carboxyaldehyde (Chasalow, F. I. et al., Steroids, 1982, 39, 617) and 3β-hydroxyandrost-5-en-17β-carboxyaldehyde (Danishefsky S. et al., J. Org. Chem., 1975, 40, 1989).

The novel compounds of general formula (II) are prepared from known compounds with methods well known to those skilled in the art.

For instance, compounds of general formula (II) wherein A represents —(CH=CH)ₙ—, n is either 1 or 2 and R¹ is H and the symbol ⌇⌇ represents either α or β configuration, are prepared from the following known compounds: methyl (E)-3β-hydroxy-5β-pregn-20-ene-21-carboxylate (Pouzar, V. et al., Collect. Czech. Chem. Commun. 1993, 58, 2963), methyl (E)-3β-hydroxypregn-20-ene-21 -carboxylate (Pouzar, V. et al., Collect. Czech. Chem. Commun. 1990, 55, 1243), methyl (E)-3β-hydroxypregn-4,20-diene-21-carboxylate (Gelbart, A. et al., J. Med. Chem., 1979, 22, 287), methyl (E)-3β-hydroxypregn-5,20-diene-21-carboxylate (Pouzar, V. et al., Collect. Czech. Chem. Commun. 1990, 55, 1243), by reduction of ester function to the corresponding alcohol function and subsequent allyl oxidation of said alcohol to an α,β-unsaturated aldehyde.

The sequence can be repeated on the suitably selected unsaturated aldehyde to obtain compounds having general formula (II) wherein n is 2 and R¹ is hydrogen and the symbol ⌇⌇ represents either α or β configuration.

For instance, the compounds of general formula (II) wherein A is —(CH=CR³)—, R¹ is hydrogen, R³ is methyl or ethyl and the symbol ⌇⌇ represents either α or β configuration, are prepared reacting the known compounds 3β-hydroxy-5β-androstan-17β-carboxyaldehyde, 3β-hydroxy-androstan-17β-carboxyaldehyde, 3β-hydroxyandrost-4-en-17β-carboxy-aldehyde, 3β-hydroxyandrost-5-en-7β-carboxyaldehyde with trimethyl 2-phosphonopropionate, triethyl 2-phosphonopropionate, trimethyl 2-phosphonobutyrate or triethyl 2-phosphonobutyrate in the presence of a base, followed by the reduction of the ester function to the corresponding alcohol function and subsequent allyl oxydation of said alcohol to an α,β-unsaturated aldehyde.

For instance, the compounds of general formula (II) wherein A is —(CH₂)ₘ—, m is either 2 or 4, R¹ is hydrogen and the symbol ⌇⌇ represents either α or β configuration are obtained by hydrogenating the corresponding compounds of general formula (II) wherein A is —(CH=CH)ₙ—, n is either 1 or 2, R¹ is hydrogen and the symbol ⌇⌇ represents either α or β configuration in the presence of a catalyst selected from e.g. palladium, platinum or nickel Raney.

The compounds of general formula (II) wherein A is —(CH$_2$)$_m$—, m is either 1 or 3, R$^1$ is hydrogen and the symbol ∼∼∼ represents either α or β configuration, are prepared from the corresponding compounds having general formula (II), wherein A is —(CH$_2$)$_m$—, and m is either 0 or 2, e.g. by chain elongation with methoxymethyltriphenylphosphonium chloride in presence of a base and subsequent acid hydrolysis; e.g. by treatment with nitromethane in presence of a base, OH removal by acetylation and reduction followed by conversion of the nitro group to nitrile and final reduction to the desired aldehyde.

Compounds of formula (II) wherein A is —(CH$_2$)m, and m is a whole number from 0 to 4; or —(CH=CH)$_n$— and n is either 1 to 2; or —(CH=CR$^3$)— and R$^3$ is methyl or ethyl, wherein R$^1$ is other than hydrogen and the symbol ∼∼∼ represents either α or β configuration are prepared from the corresponding compound (II) wherein R$^1$ is hydroxy by reaction with a compound of formula (IV)

$$R^1W \qquad (IV)$$

wherein R$^1$ has the above-specified meaning other than hydrogen, and W is an electrowithdrawing group, such as halogen, mesyloxy or tosyloxy group which imparts electrophylicity to the carbon atom it is linked to.

The reaction can be carried out in an aprotic, inert solvent such as tetrahydrofurane, dioxane, dimethylformamide, dimethyl sulfoxide or pure R$^1$W in the presence of a base, such as e.g. sodium or potassium hydride, at a temperature ranging from 0° C. to 110° C.

In all the all the foregoing conversions the aldehyde function of formula (II) is protected, if necessary, with methods well known and then removed.

The compounds of general formula (III) and (IV) are known compounds, generally available on the market or preparable from known compounds by known methods.

The compounds of general formula (I) prepared according to the invention and their pharmaceutically acceptable salts, are useful agents for the treatment of cardiovascular disorders such as heart failure and hypertension, and show reduced toxicity compared with that of positive inotropic agents, such as oubain and digitoxin.

The aforesaid compounds of general formula (I) show good affinity for the receptor site of Na$^+$, K$^+$-ATPase.

To test the affinity for the receptor site of the Na$^+$, K$^+$-ATPase and the agonist or inhibitory activity on the enzyme, the following tests were used:

a) displacement of the specific $^3$H-oubain binding from the Na$^+$, K$^+$-ATPase receptor purified according to Jorghensen (Jorghensen P., BBA, 1974, 356, 36) and Erdmann (Erdmann E. et al., Arzneim. Forsh. 1984, 34,1314);

b) inhibition of the activity of the purified Na$^+$, K$^+$-ATPase measured as % of hydrolysis of $^{32}$P-ATP in the presence and in the absence of the tested compound (Doucet A. et al., Am. J. Physiol., 1986, 251, F851).

The systolic blood pressure (SBP) and heart rate (HR) were measured by the indirect tail-cuff plethysmographic method, in four-month old pre-hypertensive male rats, (MHS or SHR), i.e. before hypertension onset, so as to register the basal value of SBP. The rats were then subdivided in groups of 7 animals each and the groups were divided in control and treated groups. The compound, suspended in 0.5% (w/v) Methocel, was orally administered daily for at least five weeks. The control group received only Methocel.

SBP and HR were measured weekly, 6 and 24 hours after the treatment.

After five weeks of treatment, when the hypertension was fully developed in the control group (nine months old rats) a one-week wash-out was conducted in order to verify whether SBP would remain low or restored to the basal values of the control group.

The reliability of this method in assessing the hypotensive activity was previously tested on β-blocking agents which did not exhibit any hypotensive activity when administered to hypertensive rats (SHR), but were effective in preventing hypertension development if administered for more than five weeks following weaning (Takeda K. et al., Japan J. Pharmacol., 1979, 29,171; Takeda K. et al., Japan J. Pharmacol., 1982, 32, 283; Richer C. et al., Eur. J. Pharmacol., 1978, 47, 393).

The affinity for and the inhibitory activity on the enzyme of some compounds of the present invention are shown in the following table:

|  | Binding $^3$H-oubain displacement $-\log IC_{50}$ | Inhibitory activity $-\log IC_{50}$ |
| --- | --- | --- |
| Comp. I-b | 6.3 | 5.1 |
| Comp. I-e | 6.8 | 5.7 |
| Comp. I-f | 5.3 | 4.1 |
| Comp. I-g | 6.6 | 5.8 |
| Comp. I-h | 6.0 | 5.3 |
| Comp. I-i | 6.2 | 5.6 |
| Comp. I-l | 5.9 | 4.6 |
| Comp. I-m | 6.4 | 5.4 |
| Comp. I-n | 5.7 | 4.7 |

The activity of some compounds in preventing the development of hypertension is shown in the following table:

| EFFECT OF 5 WEEK TREATMENT IN SPONTANEOUS HYPERTENSIVE RATS (MHS) ON THE DEVELOPMENT OF HYPERTENSION. | | | | |
| --- | --- | --- | --- | --- |
| COMPOUND | RATS | DOSE* mg/kg/os | SBP mm Hg | HR beats/min. |
| Controls | 7 | Methocel | 172+/−50 | 380+/−6.3 |
| Comp. I-g | 7 | 20 | 160+/−7.8 | 377+/−10.5 |

*In 0.5% (w/v) Methocel

The following examples illustrate the invention without limiting it.

EXAMPLE 1

(E)-17β-(2-dimethylaminoethoxyiminomethyl)-5β-androstan-3β-ol (I-a)

0.31 g of 2-dimethylaminoethoxyaniine dihydrochloride were dissolved in a solution of 0.54 g of sodium acetate in 2.8 ml of water and 4 ml of dioxane. 1N hydrochloric acid was added dropwise till pH 4.7 was reached. A solution of 0.50 g of 3β-hydroxy-5β-androstan-17β-carboxyaldehyde (Gelbart, A. et al., J. Med. Chem., 1978, 21(3), 284) in 6 ml of dioxane was slowly added dropwise and the resulting mixture was kept under stirring at room temperature for 30 minutes. The mixture was then diluted with water and extracted with methylene chloride. The organic solution was dehydrated on anhydrous sodium sulfate and evaporated to dryness under vacuum. The crude product was purified by flash-chromatography (SiO$_2$) using chloroform/methanol/ammonia 95/5/1 as eluant, to give 0.41 g of the free base of (Ib). $^1$H-NMR(300 MHz, CDCl$_3$, ppm from TMS): 0.64(3H, s); 0.91(3H,s); 2.28(6H,s); 2.65(2H,t); 3.58(1H,m); 4.10 (2H,t); 7.40(1H,d).

EXAMPLE 2

(E)-17β-[2-dimethylaminoethoxyiminomethyl]-3β-[2-(1-pirrolidinyl) ethoxy]-5β-androstane (I-b)

A solution of 0.52 g of 17β-[2-(1,3-dioxolanyl)]-3β-[2-(1-pyrrolidinyl)ethoxy]-5β-androstane (prep. 1) in 1 ml of water and 10 ml of dioxane was adjusted to pH 2 with 1N hydrochloric acid. After 4 hours at room temperature, 0.25 g of 2-dimethylaminoethoxyamine dihydrochloride were added and the resulting mixture was stirred at room temperature for one day. The dioxane was evaporated under vacuum, the residue was adjusted to pH 9 with a 5% aqueous solution of $Na_2CO_3$ and the mixture extracted with ethyl acetate. The organic solution was dehydrated over anhydrous sodium sulfate and evaporated to dryness under vacuum. The residue was purified by flash-chromatography ($SiO_2$) using chloroform/methanol/ammonia 95/5/0.5 as eluant, to give 0.38 g of free base, which was salified with a stoichiometryc amount of oxalic acid to give 0.48 g of the compound (I-b) dioxalate, as a white solid. $^1$H-NMR(300 MHZ,$CD_3OD$, ppm from TMS): 0.70(3H,s); 0.99(3H,s); 2.95(6H,s); 3.00–3.30(2H,m); 3.35–3.50(4H,m); 3.50–3.80 (5H,m); 4.31(2H,t); 7.49(1H,d).

EXAMPLE 3

(E)-17β-(2-aminoethoxyiminomethyl)-androst-4-en-3β-ol (I-c)

The compound (I-c) (0.39 g) was obtained as a white solid containing 10% of Z isomer from 0.50 g of 3β-hydroxyandrost-4-en-17β-carboxyaldehyde (Chasalow, F. I. et al., *Steroids*, 1982, 39, 617) and 2-aminoethoxyamine dihydrochloride using the same method as that described in Ex. 1.

$^1$H-NMR(300 MHz, $CDCl_3$, ppm from TMS): 0.71(3H,s); 1.00(3H,s); 3.01(2H,m); 4.14–4.26(1H,m); 4.45(2H,m), 5.32(1H,m); 6.70(0.1H,d); 7.41(0.9H,d).

EXAMPLE 4

(E)-17β-[3-(2-dimethylaminoethoxyiminomethyl)-androst-4-en-3β-ol (I-d)

The compound (I-d) (0.35 g) was obtained as a white solid, containing 10% of Z isomer from 0.50 g of 3β-hydroxyandrost-4-en-17β-carboxyaldehyde (Chasalow, F. I. et al., *Steroids*, 1982, 39, 617) and 2-dimethylaminoethoxyamine dihydrochloride using the same method as that described in Ex. 1.

$^1$H-NMR (300 MHz,$CDCl_3$, ppm from TMS); 0.70(3H,s); 1.02(3H,s); 2.82(6H,s); 3.32(2H,m); 4.14–4.26(1H,m); 4.49 (2H,m); 5.32(1H,m); 6.72(0.1H,d); 7.42(0.9H,d).

EXAMPLE 5

(E)-17β-(2-aminoethoxyiminomethyl)-androst-5-en-3β-ol (I-e)

The compound (I-e) (0.43 g) was obtained as a white solid containing 10% of Z isomer from 0.50 g of 3β-hydroxyandrost-5-en-17β-carboxyaldehyde (Danishefsky, S. et al., *J. Org. Chem.*, 1975, 40, 1989) and 2-aminoethoxyamine dihydrochloride using the same method as that described in Ex. 1.

$^1$H-NMR (300 MHZ, $CDCl_3$, ppm from TMS): 0.71(3H, s); 1.02(3H,s); 3.01(2H,m); 3.45–3.62(1H,m); 4.45(2H,m); 5.37(1H,m); 6.70(0.1H,d); 7.41(0.9H,d).

EXAMPLE 6

(E)-17β-[2-dimethylaminoethoxyiminomethyl]-androst-5-en-3β-ol (I-f)

The compound (I-f) (0.45 g) was obtained as a white solid containing 10% of Z isomer from 0.50 g of 3β-hydroxyandrost-5-en-17β-carboxyaldehyde (Danishefsky, S. et al., *J. Org. Chem.*, 1975, 40, 1989) and 2-dimethylaminoethoxyamine dihydrochloride using the same method as that described in Ex. 1.

$^1$H-NMR (300 MHz, $CDCl_3$, ppm from TMS): 0.70(3H, s); 1.02(3H,s); 2.82(6H,s); 3.31(2H,m); 3.47–3.62(1H,m); 4.48(2H,m); 5.37(1H,m); 6.72(0.1H,d); 7.42(0.9H,d).

EXAMPLE 7

(E,E)-17β-[3-(2-aminoethoxyimino)-1-propenyl]-androst-5-en-3β-ol (I-g)

The compound (I-g) (0.42 g) was obtained as a white solid containing 15% of Z isomer from 0.50 g of (E)-3β-hydroxypregna-5,20-diene-21-carboxyaldehyde (prep. 2) and 2-aminoethoxyamine dihydrochloride using the same method as that described in Ex. 1.

$^1$H-NMR (300 MHz, $CDCl_3$, ppm from TMS); 0.65(3H, s); 1.02(3H,s); 2.97(2H,m); 3.45–3.65(1H,m); 3.99–4.16 (2H,m); 5.38(1H,m); 5.95–6.18(2H,m); 7.02(0.15H,d); 7.76 (0.85H,d).

EXAMPLE 8

(E,E)-17β-[3-(2-dimethylaminoethoxyimino)-1-propenyl]-androst-5-en-3β-ol (I-h)

The compound (I-h) (0.40 g) was obtained as a white solid, containing 15% of Z isomer from 0.45 g of (E)-3β-hydroxy-pregna-5,20-diene-21 -carboxyaldehyde (prep. 2) and 2-dimethylaminoethoxyamine dihydrochloride using the same method as that described in Ex. 1.

$^1$H-NMR (300 MHz, $CDCl_3$, ppm from TMS): 0.64(3H, s); 1.02(3H,s); 2.30(6H,s); 2.60(2H,m); 3.47–3.60(1H,m); 4.15(2H,t); 5.36(1H,m); 5.92–6.17(2H,m); 7.00(0.15H,d); 7.77(0.85H,d).

EXAMPLE 9

(E,E)-17β-[3-(3-dimethylaminopropoxyimino)-1-propenyl]-androst-5-en-3β-ol (I-i)

The compound (I-i) (0.52 g) was obtained as a white solid from 0.60 g of (E)-3β-hydroxypregna-5,20-diene-21-carboxyaldehyde (prep. 2) and 2-dimethylaminopropoxyamine dihydrochloride using the same method as that described in Ex. 1.

$^1$H-NMR (300 MHz, $CDCl_3$, ppm from TMS): 0.63(3H, s); 1.01(3H,s); 2.25(6H,s); 2.35(2H,m); 3.47–3.60(1H,m); 4.05(2H,t); 5.36(1H,m); 5.90–6.06(2H,m); 7.74(1H,d).

EXAMPLE 10

(E,E)-17β-[3-(2-aminoethoxyimino)-2-methyl-1-propenyl]-androst-5-en-3β-ol (I-j)

The compound (I-j) (0.30 g) was obtained as a white solid from 0.40 g of (E)-3β-hydroxy-21-methylpregna-5,20-diene-21-carboxyaldehyde (prep. 3) and 2-dimethylaminopropoxyamine dihydrochloride using the same method as that described in Ex. 1.

$^1$H-NMR (300 MHz, $CDCl_3$, ppm from TMS): 0.66(3H, s); 1.01(3H,s); 1.71(3H,d); 3.00(2H,m) 3.45–3.65(1H,m); 4.0–4.18(2H,m); 5.37(1H,m); 5.85(1H,m); 7.75(1H,d).

EXAMPLE 11

(E)-17β[3-(2-dimethylaminoethoxyimino)propyl]-androst-5-en-3β-ol (I-k)

The compound (I-k) (0.22 g) was obtained as a white solid, containing 10% of Z isomer from 0.30 g of 3-(3β-hydroxyandrost-5-en-17β-yl)propionaldehyde (prep. 4) and 2-dimethylaminopropoxyamine dihydrochloride using the same method as that described in Ex. 1.

$^1$H-NMR (300 MHz, $CDCl_3$, ppm from TMS): 0.70(3H, s); 1.03(3H,s); 2.30(5.4H,s); 2.32(0.6H,s); 2.60(1.8H,t); 2.63(0.2H,t); 3.47–3.60(1H,m); 4.12(1.8H,t); 4.16(0.2H,t); 6.80(0.1H,t); 7.55(0.9H,t).

EXAMPLE 12
(EZ)-17β-(3-dimethylaminopropoxyiminomethyl)-androst-5-en-3β-ol (I-l)

The title compound (I-l) (0.23 g) was obtained as a white solid, mixture of 88% E isomer and 12% Z isomer, from 3β-hydroxyandrost-5-en-17β-ylcarboxyaldehyde (Danishefsky, S et al., *J. Org. Chem.*, 1975, 40, 1989) (0.25 g) and 3-dimethylaminopropoxyamine dichloride using the same procedure described in Example 1.

$^1$H-NMR (300 MHz, CDCl$_3$, ppm from TMS): 0.70(3H, s), 1.03(3H,s); 2.25(6H,s);2.31–2.40(2H,m),3.47–3.61(1H, m); 4.07(2H,t); 5.37(1H,m); 6.62(0.12H,d); 7.37(0.88H,d).

EXAMPLE 13
(E)-17β-(3-aminopropoxyiminomethyl)-androst-5-en-3β-ol (I-m)

The title compound (I-m) (0.20 g) was obtained as a light yellow solid, mixture of 92% E isomer and 8% Z isomer, from 3β-hydroxyandrost-5-en-17β-ylcarboxyaldehyde (Danishefsky, S et al., *J. Org. Chem.*, 1975, 40, 1989) (0.25 g) and 3-aminopropoxyamine dichloride using the same procedure described in Example 1.

$^1$H-NMR (300 MHz, CDCl$_3$, ppm from TMS): 0.70(3H, s); 1.03(3H,s); 2.80(2H,t), 3.46–3.60(1H,m); 4.11(2H,t); 5.37(1H,m); 6.62(0.08H,d); 7.37(0.92H,d).

EXAMPLE 14
(EZ)-17β-(4-aminobutoxyiminomethyl)-androst-5-en-3β-ol (I-n).

The title compound (I-n) (0.21 g) was obtained as a white solid, mixture of 88% E isomer and 12% Z isomer, from 3β-hydroxyandrost-5-en-17β-ylcarboxyaldehyde (Danishefsky, S et al., *J. Org. Chem.*, 1975, 40, 1989) (0.25 g) and 4-aminobutoxyamine dichloride using the same procedure described in Example 1.

$^1$H-NMR (300 MHz, CDCl$_3$, ppm from TMS): 0.70(3H, s); 1.03(3H,s); 2.72(2H,t); 3.46–3.61(1H,m); 4.04(2H,t); 5.37(1H,m); 6.62(0.12H,d); 7.36(0.88H,d).

EXAMPLE 15
(EZ)-17β-(4-dimethylaminobutoxyiminomethyl)-androst-5-en-3β-ol (I-o).

The title compound (I-o) (0.14 g) was obtained as a white solid, mixture of 88% E isomer and 12% Z isomer, from 3β-hydroxyandrost-5-en-17β-ylcarboxyaldehyde (Danishefsky, S et al., *J. Org. Chem.*, 1975, 40, 1989) (0.16 g) and 4-dimethylaminobutoxyamine dichloride using the same procedure described in Example 1.

$^1$H-NMR (300 MHz, CDCl$_3$, ppm from TMS): 0.70(3H, s); 1.03(3H,s); 2.22(6H,s); 2.29(2H,m); 3.46–3.60(1H,m); 4.05(2H,t); 5.37(1H,m); 6.61(0.12H,d); 7.36(0.88H,d).

EXAMPLE 16
[E(E,Z)]-17β-[3-(4-aminobutoxyimino)-1-propenyl]-androst-5-en-3β-ol (I-p).

The title compound (I-p) (0.14 g) was obtained as a white solid, mixture of 80% (E,E) isomer and 20% (E,Z) isomer, from (E)-3β-hydroxypregna-5,20-dien-21-carboxyaldehyde (Prep. 2) (0.15 g) and 4-aminobutoxyamine dichloride using the procedure described in Example 1.

$^1$H-NMR (300 MHz, CDCl$_3$, ppm from TMS): 0.63(3H, s); 1.03(3H,s); 2.74(2H,t); 3.46–3.62(1H,m); 4.09(2H,m); 5.37(1H,m); 5.92–6.17(2H,m); 6.99(0.2H,d); 7.71(0.8H,d).

Preparation 1
17β-[2-(1,3-dioxolanyl)]-3β-[2-(1-pyrrolidinyl)ethoxy]-5β-androstane (II-a)

A mixture of 2.50 g of 3β-hydroxy-5β-androstan-17β-carboxyaldehyde (Gelbart, A. et al., *J. Med. Chem.*, 1978, 21(3), 284), 4.50 ml of ethylene glycol and 0.30 g of oxalic acid in 50 ml of acetonitrile was kept under stirring at room temperature for 3 hours. The mixture was then diluted with a 5% aqueous solution of sodium bicarbonate and extracted with ethyl acetate. The organic solution was dehydrated over anhydrous sodium sulfate and evaporated to dryness under vacuum to give 2.66 g of 17β-[2-(1,3-dioxolanyl)]-5β-androstan-3β-ol.

$^1$H-NMR (300 MHz, CDCl$_3$, ppm from TMS): 0.72(3H, s); 0.98(3H,s); 3.70–4.00(4H,m); 4.11(1H,m); 4.71(1H,d).

A mixture of 2.56 g of 17β-[2-(1,3-dioxolanyl)]-5β-androstan-3β-ol, 14.70 g of 1-(2-chloroethyl)pyrrolidine and 3.30 g of sodium hydride (55% suspension in mineral oil) in 110 ml of anhydrous tetrahydrofurane was kept at the reflux temperature for 12 hours. The mixture was cooled, water was added thereto and the resulting mixture was extracted with ethyl acetate. The organic solution was dehydrated over anhydrous sodium sulfate and evaporated to dryness under vacuum. The crude product was purified by flash-chromatography (SiO$_2$) using chloroform/methanol 95/5 as eluant, to give 1.90 g of (II-a) as an oil.

$^1$H-NMR (300 MHz, CDCl$_3$, ppm from TMS): 0.71(3H, s); 0.91(3H,s); 2.60–2.80(4H,m); 2.76(3H,t); 3.60–3.65(3H, m), 3.75–4.00(4H,m); 4.71(1H,d).

Preparation 2
(E)-3β-hydroxypregna-5,20-diene-21-carboxyaldehyde (II-b)

To a solution of 4.85 g of methyl (E)-3β-hydroxypregna-5,20-diene-21-carboxylate (Pouzar, V. et al., *Collect. Czech. Chem. Commun*, 1990, 55,1243), in 200 ml of anhydrous tetrahydrofurane, 81 ml of i-Bu$_2$AlH (1M) in hexane were added dropwise in a nitrogen atmosphere at −78° C. After two hours the reaction mixture was treated with an aqueous solution of citric acid (30 g in 100 ml of water). The mixture was filtered on Celite and the residue washed with ethyl acetate. The organic solution was dehydrated over anhydrous sodium sulfate and evaporated to dryness under vacuum, to give 4.25 g of (E)-21-hydroxymethylpregna-5,20-dien-3β-ol as a white solid.

$^1$H-NMR (300 MHz, CDCl$_3$, ppm from TMS): 0.62(3H, s); 1.05 (3H,s); 3.47–3.60(1H,m); 4.13(2H,d); 5.38(1H,m); 5.65(2H,m).

To a solution of 4.25 g of (E)-21-hydroxymethylpregna-5,20-dien-3β-ol in 150 ml of chloroform, 11 g of MnO$_2$ were added at room temperature. The solution was kept under stirring overnight, then the mixture was filtered on Celite. The organic solution was dehydrated over anhydrous sodium sulfate and evaporated to dryness under vacuum to give 3.89 g of compound (II-b) as a white solid.

$^1$H-NMR (300 MHz, CDCl$_3$, ppm from TMS): 0.70(3H, s); 1.03(3H,s); 3.46–3.61(1H,m); 5.37(1H,m); 6.08–6.17 (1H,dd), 6.80–6.90(1H,dd); 9.52(1H,d).

Preparation 3
(E)-3β-hydroxy-21-methylpregna-5,20-diene-21-carboxyaldehyde (II-c)

To a mixture of 1.20 g of sodium hydride (55% suspension in mineral oil) in 100 ml of anhydrous THF, 6.9 ml of triethyl 2-phosphonopropionate were added dropwise at 0° C. The mixture was stirred at room temperature for 30 min, then 4.80 g of 3β-hydroxyandrost-5-en-17β-carboxyaldehyde (Danishefsky, S. et al., *J. Org. Chem.*, 1975, 40, 1989) in 50 ml of THF were added dropwise. After 2 hours the mixture was diluted with 200 ml of a 5% aqueous solution of NaH$_2$PO$_4$; the organic phase was separated and the aqueous phase was extracted with ethyl acetate. The organic solution was dehydrated over anhydrous sodium sulfate and evaporated to dryness under vacuum. The product was purified by flash chromatography (SiO$_2$) using ciclohexane/ethyl acetate 1/1 as eluant, to give 4.65 g of ethyl (E)-3β-hydroxy-21-methylpregna-5,20-diene-21-carboxylate as a white solid.

$^1$H-NMR (300 MHz, CDCl$_3$, ppm from TMS): 0.65(3H, s); 1.00(3H,s); 1.30(3H,t); 1.85(3H,d); 3.46–3.60(1H,m); 4.20(2H,q); 5.37(1H,d); 6.70–6.80(1H,m).

From 4.50 g of ethyl (E)-3β-hydroxy-21-methylpregna-5,20-diene-21-carboxylate, 3.05 g of (II-c) were obtained as a white solid, using the same method as that described in prep. 2.

$^1$H-NMR (300 MHZ, CDCl$_3$, ppm from TMS): 0.70(3H, s); 1.03(3H,s); 1.80(3H,s); 3.46–3.61(1H,m); 5.37(1H,m); 6.50–6.60(1H,m); 9.42(1H,s).

Preparation 4
3-(3β-hydroxyandrost-5-en-17β-yl)propionaldehyde (II-d)

A mixture of 6.00 g of (E)-3β-hydroxypregna-5,20-diene-21-carboxylaldehyde (II-c) and 1.20 g of 5% palladium on charcoal in 1.20 L of ethanol was hydrogenated at room temperature and atmospheric pressure for 30 minutes. The mixture was then filtered on Celite and the ethanol evaporated to dryness under vacuum to give 5.83 g of compound (II-d) as a white solid.

$^1$H-NMR (300 MHz, CDCl$_3$, ppm from TMS): 0.97(3H, s); 0.98(3H,s); 2.20–2.55(2H,m); 3.50–3.60(1H,m); 5.35 (1H,m); 9.70(1H,m).

We claim:
1. A 17-hydroxyiminoalkyl or 17-hydroxyiminomethylalkenyl cyclopentaneperydrophenanthrene of general formula (I):

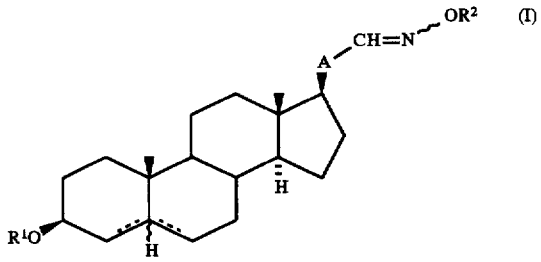

wherein:
the symbol ~~~ represents either α or β configuraton or a Z or E configuration;
A represents (CH$_2$)m, —(CH=CH)n— or —(CH=CR$^3$)—;
m is a whole number from 0 to 4;
n is either 1 or 2;
R$^3$ represents methyl, ethyl or n-propyl;
R$^1$ is H or C2–C4 alkyl unsubstituted or substituted by NR$^4$R$^5$
wherein
R$^4$ and R$^5$ are independently H, C1–C4 alkyl, or R$^4$ and R$^5$ can form with the nitrogen atom they are linked to, a saturated or unsaturated five- or six-membered mono-heterocyclic ring optionally containing a further heteroatom selected from N and O;
R$^2$ represents C2–C4 alkyl, unsubstituted or substituted by NR$^4$R$^5$ or
NHC(=NH)NH$_2$, wherein R$^4$ and R$^5$ have the above-specified meaning.

2. A stereoisomer, Z or E isomer or mixtures thereof, an optical isomer or mixtures thereof, or a pharmaceutically acceptable salt of the compound of general formula (I)

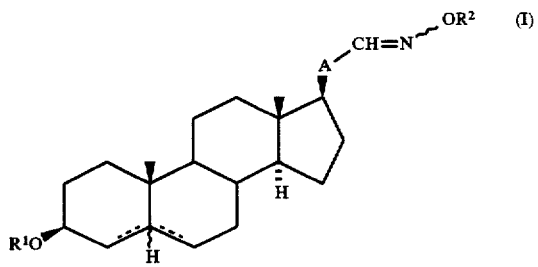

wherein:
the symbol ~~~ represents either α or β configuration or a Z or E configuration;
A represents (CH$_2$)m, —(CH=CH)n— or —(CH=CR$^3$)—;
m is a whole number from 0 to 4;
n is either 1 or 2;
R$^3$ represents methyl, ethyl, or n-propyl;
R$^1$ is H or C2–C4 alkyl unsubstituted or substituted by NR$^4$R$^5$
wherein
R$^4$ and R$^5$ are independently H, C1–C4 alkyl, or R$^4$ and R$^5$ can form with the nitrogen atom they are linked to, a saturated or unsaturated five- or six-membered mono-heterocyclic ring optionally containing a further heteroatom selected from N and O;
R$^2$ represents C2–C4 alkyl, unsubstituted or substituted by NR$^4$R$^5$ or NHC(=NH)NH$_2$, wherein R$^4$ and R$^5$ have the above-specified meaning.

3. A compound according to claim 1 which is selected from:

(E)-17β-(2-aminoethoxyiminomethyl)-5β-androstan-3β-ol (E)-17β-(3-aminopropoxyiminomethyl)-5β-androstan-3β-ol (E)-17β-(4-aminobutoxyiminomethyl)-5β-androstan-3β-ol (E)-17β-(2-dimethylaminoethoxyiminomethyl)-5β-androstan-3β-ol (E)-17β-(3-dimethylaminopropoxyiminomethyl)-5β-androstan-3β-ol (E)-17β-(4-dimethylaminobutoxyiminomethyl)-5β-androstan-3β-ol (E)-17β-(2-guanidinoethoxyiminomethyl)-5β-androstan-3β-ol (E)-17β-(3-guanidinopropoxyiminomethyl)-5β-androstan-3β-ol (E,E)-17β-[3-(2-aminoethoxyimino)-1-propenyl]-5β-androstan-3β-ol (E,E)-17β-[3-(3-aminopropoxyimino)-1-propenyl]-5β-androstan-3β-ol (E)-17β-[3-(4-aminobutoxyimino)-1-propenyl]-5β-androstan-3β-ol (E,E)-17β-[3-(2-dimethylaminoethoxyimino)-1-propenyl]-5β-androstan-3β-ol (E,E)-17β-[3-(3-dimethylaminopropoxyimino)-1-propenyl]-5β-androstan-3β-ol (E,E)-17β-[3-(2-guanidinoethoxyimilno)-1-propenyl]-5β-androstan-3β-ol (E,E)-17β-[3-(3-guanidinopropoxyimino)-1-propenyl]-5β-androstan-3β-ol (E,E)-17β-[3-(2-aminoethoxyimino)-2-methyl-1-propenyl-5β-androstan-3β-ol (E,E)-17β-[3-(3-aminopropoxyimino)-2-methyl-1-propenyl]-5β-androstan-3β-ol (E,E)-17β-[3-(2-dimethylaminoethoxyimino)-2-methyl-1-propenyl]-5β-androstan-3β-ol (E,E)-17β-[3-(3-dimethylaminopropoxyimino)-2-methyl-1-propenyl-5β-androstan-3β-ol (E,E)-17β-[3-(2-guanidinoethoxyimino)-2-methyl-1-propenyl]-5β-androstan-3β-ol (E,E)-17β-[3-(3-guanidinopropoxyimino)-2-methyl-1-propenyl]-5β-androstan-3β-ol (E,E)-17β-[3-(2-aminoethoxyimino))-2-ethyl-1-propenyl]-5β-androstan-3β-ol (E,E,E)-17β-[5-(2-aminoethoxyimino)-1,3-pentadienyl]-5β-androstan-3β-ol (E,E,E)-17β-[5-(3-aminopropoxyimino)-1,3-pentadienyl]-5β-androstan-3β-ol (E,E,E)-17β-[5-(2-dimethylaminoethoxyimino)-1,3-pentadienyl]-5β-androstan-3β-ol (E,E,E)-17β-[5-(3-dimethylaminopropoxyimino)-1,3-pentadienyl]-5β-androstan-3β-ol (E,E,E)-17β-[5-(2-guanidinoethoxyimino)-1,3-pentadienyl]-5β-androstan-3β-ol (E,E,E)-17β-[5-(3-guanidinopropoxyimino)-1,3-pentadienyl]-5β-androstan-3β-ol (E)-17β-[2-(2-aminoethoxyimino)ethyl]-5β-androstan-3β-ol (E)-17β-[2-(3-aminopropoxyimino)ethyl]-5β-androstan-3β-ol (E)-17β-[2-(2-dimethylaminoethoxyinmino)ethyl]-5β-androstan-3β-ol (E)-17β-[2-(3-dimethylaminopropoxyimino)ethyl]-5β-androstan-3β-ol (E)-17β-[2-(2-guanidinoethoxyimino)ethyl]-5β-androstan-3β-ol (E)-17β-[2-(3-guanidinopropoxyimino)ethyl]-5β-androstan-3β-ol (E)-17β-[3-(2-aminoethoxyimino)propyl]-5β-androstan-3β-ol (E)-17β-[3-(3-aminopropoxyimino)propyl]-5β-androstan-3β-ol (E)-17β-[3-(2-dimethylaminoethoxyimino)propyl]-5β-androstan-3β-ol (E)-17β-[3-(3-dimethylaminopropoxyimino)propyl]-5β-androstan-3β-ol (E)-17β-[3-(2-guanidinoethoxyimino)propyl]-5β-androstan-3β-ol (E)-17β-[3-(3-guanidinopropoxyimino)propyl]-5β-androstan-3β-ol an E or Z isomer, a mixture of said isomers, a corresponding androstan 3β-ol, androst-4-en-3β-ol or androst-5-en-3β-ol of the aforesaid compounds, and a corresponding 3β-(2-aminoethyl), 3β-(2-dimethylaminoethyl), 3β-(2-(1-pyrrolidinyl)ethyl), 3β-(3-aminopropyl), 3β-(3-dimethylaminopropyl) or 3β-(3-(1-pyrrolidinyl)propyl) ether of the aforesaid compounds.

4. A process for the preparation of compounds of general formula (I), which comprises a condensation reaction of compounds of general formula (II)

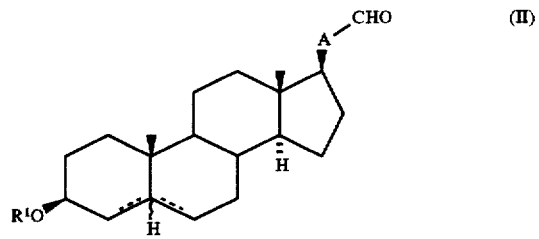

wherein A, $R^1$ and the symbol ⁓ are as defined in claim 1, with compounds of general formula (III)

$H_2NOR^2$ (III)

wherein $R^2$ is as defined in claim 1, to give the compounds of general formula (I).

5. A pharmaceutical composition comprising a compound of formula (I) as defined in claim 1 and a pharmaceutically acceptable excipient therefor.

6. A compound according to claim 1, which is (E)-17β-(2-aminoethoxyiminomethyl)-androst-5-en-3β-ol.

* * * * *